(12) United States Patent
Bulla, Jr. et al.

(10) Patent No.: US 6,759,230 B1
(45) Date of Patent: Jul. 6, 2004

(54) MICROBE, MICROBIAL EXOPOLYSACCHARIDE, AND USES THEREOF

(75) Inventors: Lee A. Bulla, Jr., Tioga, TX (US); Mehmet Candas, Dallas, TX (US)

(73) Assignee: The Board of Regents, The University of Texas, Austin, TX (US)

( * ) Notice: Subject to any disclaimer, the term of this patent is extended or adjusted under 35 U.S.C. 154(b) by 0 days.

(21) Appl. No.: 09/696,929

(22) Filed: Oct. 25, 2000

Related U.S. Application Data (60) Provisional application No. 60/161,588, filed on Oct. 26, 1999.

(51) Int. Cl.[7] .................................................. C12N 1/20
(52) U.S. Cl. ..................... 435/252.1; 435/243; 435/245; 435/259; 435/101
(58) Field of Search ................................. 435/243, 245, 435/252.1, 259, 101

(56) References Cited

U.S. PATENT DOCUMENTS

| | | | |
|---|---|---|---|
| 3,974,179 A | * | 8/1976 | Demerson et al. ...... 260/326.28 |
| 4,806,636 A | | 2/1989 | Harris et al. ................. 536/123 |
| 4,923,442 A | | 5/1990 | Segall et al. ................... 604/52 |
| 5,130,230 A | | 7/1992 | Segall et al. .................... 435/1 |
| 5,229,277 A | | 7/1993 | Day et al. ..................... 435/103 |
| 6,046,020 A | * | 4/2000 | Bochner et al. ............... 435/31 |

OTHER PUBLICATIONS

Chung et al, Current Microbiology 35: 195–200, 1997.*
Chowdhury et al, Med. Sci Res. 24: 801–802, 1996.*
Doyle (ed.), Methods in Enzymology, vol. 310, Biofilms, Academic Press (1999).
El–Falaha et al., Egyptian Journal of Pharmaceutical Sciences (1998) 39(1–3):1–17.
Ohtani et al., Bioscience Biotechnology and Biochemistry (1995) 59(9):1628–1631.
Scamparini et al., International Journal of Biological Macromolecules (1997) 21(1–2):115–121.

* cited by examiner

*Primary Examiner*—Francisco Prats
(74) *Attorney, Agent, or Firm*—Morrison & Foerster LLP (57) ABSTRACT

A novel microorganism producing a nontoxic, non-antigenic exopolysaccharide is taught. The exopolysaccharide has neutral sugars migrating at the same rate as mannose, fucose, fructose and galactose, acidic sugars migrating at the same rate as fucose and amine sugars migrating at the same rate as glucose and fucose, and wherein the ratio of galactose:fucose:glucose:mannose is about 1:2:3:6. The microbe and the exopolysaccharide have uses as a biofilm in geologic applications and have several consumer uses as food and drug polymers and use as a plasma extender.

8 Claims, 10 Drawing Sheets

Figure 1

Figure 2 exponential phase

Figure 3 stationary phase

Lanes 1 & 4: M.W. stds.

Lanes 2 & 5: UTD-001

Lanes 3 & 6: *B. indica* 9038

| RT | Area | Ar/HT | Respn | ECL | Name | % | Comment 1 | Comment 2 |
|---|---|---|---|---|---|---|---|---|
| 1.681 | 412383000 | 0.030 | ***** | 7.006 | SOLVENT PEAK | **** | < min rt | |
| 1.794 | 16776 | 0.024 | ***** | 7.227 | ******************** | **** | < min rt | |
| 2.241 | 750 | 0.044 | ***** | 8.104 | ******************** | **** | < min rt | |
| 2.300 | 1326 | 0.044 | ***** | 8.104 | ******************** | **** | < min rt | |
| 2.347 | 504 | 0.032 | ***** | 8.219 | ******************** | **** | < min rt | |
| 3.849 | 1128 | 0.028 | 1.102 | 8.312 | Sum In Feature 3 | 0.15 | ECL deviates 0.002 | 12:0 ALDE? |
| 4.833 | 25458 | 0.031 | 1.052 | 10.916 | 12:0 | 3.34 | ECL deviates - 0.000 | Reference - 0.004 |
| 5.989 | 4578 | 0.038 | 1.015 | 12.000 | 13:0 | 0.58 | ECL deviates 0.000 | Reference - 0.003 |
| 7.102 | 1032 | 0.043 | ***** | 13.000 | ******************** | **** | | |
| 7.296 | 4584 | 0.050 | 0.986 | 13.813 | unknown 13.961 | 0.56 | ECL deviates - 0.007 | |
| 7.358 | 4584 | 0.039 | 0.985 | 13.813 | 14:0 | 6.74 | ECL deviates - 0.001 | Reference - 0.004 |
| 8.080 | 54882 | 0.040 | 0.974 | 13.954 | Sum In Feature 2 | 0.50 | ECL deviates - 0.001 | 13:0 3OH/15:1 i i/H |
| 8.130 | 41344284 | 0.039 | 0.973 | 13.999 | unknown 14.503 | 0.52 | ECL deviates - 0.002 | |
| 8.576 | 810 | 0.038 | 0.967 | 14.469 | 15:1 w8c | 0.10 | ECL deviates - 0.001 | |
| 8.897 | 32478 | 0.041 | 0.963 | 14.501 | 15:0 | 3.90 | ECL deviates - 0.000 | Reference - 0.004 |
| 9.189 | 1974 | 0.043 | ***** | 14.791 | ******************** | **** | | |
| 9.704 | 58386 | 0.044 | 0.955 | 15.000 | Sum In Feature 3 | 6.95 | ECL deviates - 0.003 | 16:1 ISO I/14:0 3OH |
| 10.259 | 183384 | 0.044 | 0.950 | 15.176 | Sum In Feature 4 | 21.7 | ECL deviates - 0.002 | 16:1 w7c/15 iso 2OH |
| 10.407 | 1512 | 0.043 | 0.948 | 15.908 | 15:1 w5c | 8.18 | ECL deviates - 0.000 | |
| 10.562 | 212406 | 0.044 | 0.947 | 16.002 | 16:0 | 25.0 | ECL deviates - 0.002 | Reference - 0.002 |
| 10.715 | 1074 | 0.064 | ***** | 16.091 | ******************** | **** | | |

*FIG. 4A*

| RT | Area | Ar/HT | Respn | ECL | Name | % | Comment 1 | Comment 2 |
|---|---|---|---|---|---|---|---|---|
| 11.425 | 1188 | 0.041 | 0.941 | 16.502 | 15:0 3OH | 0.14 | ECL deviates - 0.002 | |
| 11.924 | 3132 | 0.051 | 0.938 | 16.792 | 17:1 w8c | 0.37 | ECL deviates - 0.000 | |
| 12.091 | 87876 | 0.048 | 0.937 | 16.889 | 17:) CYCLO | 10.2 | ECL deviates - 0.001 | Reference - 0.003 |
| 12.282 | 14676 | 0.046 | 0.936 | 17.000 | 17:0 | 1.71 | ECL deviates - 0.000 | Reference - 0.004 |
| 13.598 | 996 | 0.050 | ***** | 17.750 | ********************* | **** | | |
| 13.725 | 146304 | 0.048 | 0.929 | 17.822 | Sum In Feature 7 | 16.9 | ECL deviates - 0.000 | 18:1 w7c/w9t/w12t |
| 14.032 | 1122 | 0.044 | 0.928 | 17.997 | 18:0 | 0.13 | ECL deviates - 0.003 | Reference - 0.007 |
| 14.797 | 1242 | 0.057 | ***** | 18.437 | ********************* | **** | | |
| 14.986 | 822 | 0.053 | ***** | 18.546 | ********************* | **** | | |
| 15.605 | 1446 | 0.048 | 0.923 | 18.901 | 19:0 CLYCL w8c | 0.17 | ECL deviates - 0.001 | Reference - 0.003 |
| 15.888 | 480 | 0.045 | ***** | 19.065 | ********************* | **** | | |
| 19.033 | 690 | 0.042 | ***** | 20.888 | ********************* | **** | >max rt | |
| 19.715 | 90 | 0.033 | ***** | 21.284 | ********************* | **** | >max rt | |
| ****** | 4134 | ***** | ***** | ****** | SUMMED FEATURE 2 | 0.50 | 15:1 ISO H/13:0 3OH | 13:0 3OH/15:1 i I/H |
| ****** | ***** | ***** | ***** | ****** | ********************* | **** | 15:1 ISO I/13:0 3OH | unknown 10.928 |
| ****** | 59514 | ***** | ***** | ****** | SUMMED FEATURE 3 | 7.10 | 12:0 ALDE ? | 14:0 3OH/16:1 ISO I |
| ****** | ***** | ***** | ***** | ****** | ********************* | **** | 16:1 ISO I/14:0 3OH | 15:0 ISO 2OH/16:1w7c |
| ****** | 183384 | ***** | ***** | ****** | SUMMED FEATURE 4 | 21.7 | 16:1 w7c/15 iso 2OH | 18: w9c/w12t/w7c |
| ****** | 146304 | ***** | ***** | ****** | SUMMED FEATURE 7 | 16.9 | 18:1 w7c/w9t/w12t | |
| ****** | ***** | ***** | ***** | ****** | ********************* | **** | 18:1 w12t/w9t/w7c | |

FIG. 4B

| Solvent Ar | Total Area | Named Area | % Named | Total Amount | Nbr | ECL Deviation | Ref ECL Shift |
|---|---|---|---|---|---|---|---|
| 41238300 | 851388 | 843768 | 99.10 | 802384 | 9 | 0.002 | 0.004 |

TSBA (Rev.3.90) K.luyvera .................................................... 0.835
    K. cryocrescens ........................................ 0.835
    K. ascorbata ............................................. 0.528
Enterobacter .................................................................. 0.753
    E. taylorae ................................................ 0.753
    E. asburiae* ............................................. 0.510
    E. cloacae* ............................................... 0.397 (excludes ATCC 35549 which is atypical
Salmonella ..................................................................... 0.521
    S. choleraesuis ........................................ 0.521
        S.c. arizonae .................................... 0.521
        S.c. choleraesuis ............................ 0.421
    S. bongori ................................................. 0.275
    S. typhimurium ....................................... 0.267
        S. t. GC subgroup B ....................... 0.267
        S. t. Gc subgroup A ....................... 0.182

MICROBE, MICROBIAL EXOPOLYSACCHARIDE, AND USES THEREOF

CROSS-REFERENCES TO RELATED APPLICATIONS

This Application for Patent claims the benefit of priority from, and hereby incorporates by reference the entire disclosure of, co-pending U.S. Provisional Application for Patent Serial No. 60/161,588 filed Oct. 26, 1999.

TECHNICAL FIELD OF THE INVENTION

The present invention relates in general to a novel non-pathogenic microbe that produces a nontoxic, non-antigenic exopolysaccharide. The use of the microbe and exopolysaccharide in environmental engineering, agricultural, geologic, consumer and medical applications is described. Inhibition and control of mucoidy exopolysaccharide is also described.

BACKGROUND OF THE INVENTION

The invention pertains to a novel non-pathogenic microbe that produces a non-toxic, non-antigenic exopolysaccharide. The exopolysaccharide can be used as a biofilm in environmental engineering and agricultural applications and as a filler or polymer in consumer and medical applications. Biofilm applications are described first, then particular medical applications are described.

The term "biofilm" is used to describe an organic material that includes microorganisms embedded in a polymer matrix of their own making. The matrix consists largely of exopolysaccharides and is a tough, elastic, mucoidal material that adheres strongly to soil particles. Growth of a biofilm in a sandy soil is achieved by injecting a bacterial and nutrient solution into soil specimens. The resulting biofilm treatment is used to clog soil pores, thereby reducing the ability of the soil to transmit fluids.

Examples of biofilms are produced by certain strains of *Klebsiella pneumoniae* and Pseudomonas species. A problem with the use of *K. pneumoniae* is that Klebsiella is a genus that includes a number of human pathogens. Furthermore, the pathogenicity of *K. pneumoniae* itself is associated with its ability to create a mucoidal exopolysaccharide used in attachment and colonization that helps the pathogen evade both the non-specific and specific immune clearing defensive mechanisms.

Another example of a biofilm is described in U.S. Pat. No. 4,800,959, by Costerton, which discloses the use of a microbial process for selectively plugging a subterranean formation. In the process taught, a highly permeable stratum or zone in a subterranean reservoir is plugged using Klebsiella or Pseudomonas bacteria that were starved to reduce their size prior to being injected into the target zone. The bacteria regain full cell size, proliferate and commence production of biofilm-forming exopolysaccharides upon exposure to minimal nutrient containing media. The biofilm produced by these bacteria selectively seal off the high permeability zones of a formation and reduce aqueous flow through the zone.

In addition to the above described biofilm uses, there has been a need for perfusion solutions and blood substitutes. Currently available and approved compounds, however, have so far failed to meet the increasing demands on our blood provider system. A number of blood substitutes have been developed over the last few years to attempt to meet the increasing demand for blood, blood substitutes and plasma expanders. Unfortunately, many of the plasma expanders that are currently in use fail as the small molecules on which they depend to provide osmotic pressure readily traverse capillary beds as a consequence of the negative osmotic pressure found in post-arterial capillary beds. The loss of osmotic potential, makes the long-term use of current plasma expanders for maintaining proper ionic or fluid balance or plasma volume in a mammalian subject unsatisfactory.

Those blood substitutes that have an impermeable substance to maintain volume use human serum albumin or a mixture of plasma proteins as the oncotic agent. These substitute plasma proteins depend on the same blood and plasma supply as our current blood provider system, therefore failing to meet the increased demand for these products.

A number of patents have issued to Segall that are directed to blood and plasma substitutes. U.S. Pat. No. 4,923,442, and the reissue thereof, discloses a number of solutions used in blood substitution of living subjects all of which include at least some concentration of a cardioplegia agent, usually potassium ion. U.S. Pat. No. 4,923,442 discloses surgical methods, particularly in respect to instrument placement and the control of pulmonary wedge pressure generally applicable to perfusion of subjects. U.S. Pat. No. 5,130,230 discloses a blood substitute that may be used as a system of solutions in which a number of solutions, are used sequentially to completely replace the blood of living subjects. U.S. Pat. No. 5,130,230 discloses that the blood substitute comprises "an aqueous solution of electrolytes at physiological concentration, a macromolecular oncotic agent, a biological buffer having a buffering capacity in the range of physiological pH, simple nutritive sugar or sugars, and magnesium ion in a concentration sufficient to substitute for the flux of calcium across cell membranes."

In addition to the patented inventions described above, a number of commercially available products have been used for the treatment of hypovolemic patients. These include: HESPAN™ (6% hetastarch in 0.9% sodium chloride injection, PENTASPAN™ (10% pentastarch in 0.9% sodium chloride injection [both by DUPONT PHARMACEUTICALS™, Wilmington Del.]), MACRODEX™ (6% dextran 70 in 5% dextrose injection or 6% dextran 70 in 0.9% sodium chloride injection [PHARMACIA, INC.™, Piscataway, N.J.]) and RHEOMACRODEX™ (10% dextran 40 in 5% dextrose injection or 10% dextran 40 in 0.9% sodium chloride injection [PHARMACIA, INC.™, Piscataway, N.J.]). All of these products, however, depend on compounds that are polymeric and that often dissociate or are broken down by natural physiologic enzymes with time. Alternatively, bacteria may take advantage of these newly supplied nutrient sources, causing severe septicemia in patients that are infected by pathogens at the time of injury. Thus, a need remains for a better oncotic agent.

The ability to produce mucoidal exopolysaccharides in medically important bacteria is critical to attachment to surfaces, resulting in increased resistance to drug treatments. Both chemical and physical treatments have been developed to control biofilm formation. *Methods in Enzymology*, Vol. 310, Biofilms, Ed. Ron J. Doyle, Academic Press, 1999. However, because biofilms are associated with pathogenicity, persistent and resistant bacterial infections and bio-corrosion of industrial structures, there is need for additional simple and efficient methods to control biofilms.

SUMMARY OF THE INVENTION

The newly discovered bacterium LAB-1, deposited at ATCC No. PTA-2500, possesses a number of potential commercial biofilm applications. These include, but are not limited to: (1) subsurface biofilm cutoff wall formation; (2) subsurface liners that include compacted, biofilm treated soil; (3) in-situ biofilm liners; (4) barriers made by treating geotextiles with biofilm materials; (5) improved ability of sand to retain moisture; (6) reclamation of poor soils and conversion into agriculture land; (7) significantly increased soil biomass in the form of polymers that function as a nutrient supply for plant growth and/or help retain nutrients and water; and (8) providing cohesion to otherwise cohesionless soils (such as sand dunes), thus making the soil more resistant to erosion by wind and/or water.

It has been found that the prior art methods and biofilms fail to provide biologically and environmentally safe and efficacious water, soil and waste retention characteristics. A significant problem with existing technology is the pathogenicity of the bacteria used to produce the biofilms. The present invention, therefore, is directed to a non-pathogenic bacterium that produces a biofilm made of exopolysaccharide that is essentially made of neutral sugars that migrate at the same rate as: mannose, fucose, fructose and galactose, acidic sugars that migrate at the same rate as fucose and amine sugars that migrate at the same rate as glucose and fucose.

More particularly, the bacterium is a LAB-1 strain. The biofilm producing bacterium may be further defined as being capable of growth between about pH 4 and 11 and between about 15° and 45° C. The LAB-1 strain is capable of growth in minimal growth media, or may be grown in an aqueous nutrient medium that includes yeast, peptone and mineral salt ingredients. LAB-1 is a gram-negative, rod-shaped bacterium of about 0.2×0.8 $\mu$m that secretes the exopolysaccharide described herein.

In one embodiment of the present invention, the LAB-1 strain is used in plugging a permeable subterranean stratum by providing LAB-1 bacteria in a nutrient-containing solution into the target stratum. The nutrient-containing solution is generally adapted to provide substantial and uniform growth conditions for the LAB-1. Sufficient biofilm is produced under these conditions to effectively plug the stratum. For example, the bacterium in situ can yield a saturated hydraulic conductivity equal to or less than 1.5× $10^-$ cm/sec, equal to or less than 1.0×$10^-$ cm/sec or even equal to or less than 1.5×$10^-$ cm/sec.

Alternatively, the bacteria may be preincubated in culture in an aqueous suspension medium with agitation for an incubation period sufficient to initiate bacterial exopolysaccharide production before injection into the stratum. The method of plugging the subterranean stratum may also include draining nutrient deficient suspension medium from the reservoir, and recharging the reservoir with aqueous nutrient medium to maintain bacterial growth for an elapsed time period sufficient to establish a biofilm of prescribed saturated hydraulic conductivity. The draining and recharging steps with aqueous nutrient medium may be conducted at least once every 48 hours of elapsed time period. The step of pre-incubating the bacteria may be, e.g., for at least about 72 hours. These growth conditions permit for the establishment of a biofilm having a population between about 10–10 bacterial Colony Forming Units per square centimeter on a slide surface.

The biofilm may be used to plug open conduits, deposited in a subsurface biofilm cutoff wall, used to enhance the water retaining ability of subsurface liners or even for improving the water retention capabilities of compacted, semi-compacted or loosened biofilm treated soil. When used in a liner, the biofilm may be deposited in-situ. The biofilm may also be used along with and/or to enhance environmental barriers by treating geotextiles with the biofilm.

Another important aspect of this polymer is its lack of antigenicity and toxicity in an animal system. This suggests several consumer/medical applications, including: (1) use a food additive or food thickening or filler agent; (2) use as plasma expander; (3) use in polymer industry; (4) use as chromatography matrix support for purification of chemicals; (5) use in scientific research as suspension solution instead of ficoll and the like; (6) use in determining the gene content of the organism, especially those coding for the biosynthesis of the exopolysaccharide polymer; (7) use of the polymer materials in the cosmetic field; (8) use to augment insect or animal diets; (9) use as an additive in tissue culture media; (10) for use as a semi-solid to solid matrix, e.g, gel electrophoresis; (11) for use as an additive in toothpaste, ointments, creams and lotions; (12) for mixing with dyes, stains, paints and varnishes; (13) for inclusion in dialysis; (14) for use in composite materials, e.g., bricks, tile, mortars; (15) for use as part of a sealant; (16) viscosity modifier for oils, waxes & greases; (17) use as a filler, thickener or extender in pharmaceutical preparations; (18) use of the polymer in bioscaffolding applications, including wound-healing applications; and (19) use as a bacteriostatic (biostat) agent to inhibit or at least fail to support bacterial growth, and even possibly as a biocide.

In particular, a compound is needed for use as a plasma extender that serves to increase blood volume and that is impermeable at blood capillaries. The compound must not readily dissociate or be rapidly broken down by natural physiologic enzymes with time. Furthermore, the compound and its use as a plasma expander must not provide bacteria with an exogenous nutrient source, which may lead to accentuating already severe septicemia in patients that are infected by pathogens at the time of the injury that is causing hypovolemia.

More particularly, the present invention is an exopolysaccharide produced by the LAB-1 bacterial stain. The exopolysaccharide does not appear to easily support bacterial growth. This was determined by testing the ability of *E. coli* or *S. indica* to grow on the exopolysaccharide and no growth was observed. Further, the exopolysaccharide is not antigenic as tested by injection into mice. Thus, the product appears to satisfy some of the basic parameters required for a plasma expander.

The exopolysaccharide is secreted into the cell culture medium and collected for use in, e.g., a plasma expander. When used as a plasma expander alone, or in combination with other elements, the exopolysaccharide will be provided in an isotonic solution. In one embodiment, a blood-free plasma expander and blood substitute for use in a subject in need thereof includes a single solution with at least two water soluble oncotic agents, one of which is a water soluble polysacoharide oncotic agent and one of which is serum albumin, wherein the exopolysaccharide consisting essentially of mannose, fucose, fructose and galactose, acidic fucose and amine containing glucose and fucose.

The plasma expander and blood substitute may have a ratio of water soluble exopolysaccharide oncotic agent to serum albumin between 1:1 and 1:2, weight to weight. The combined percentage of water-soluble exopolysaccharide oncotic agent and serum albumin in a solution of the plasma expander and blood substitute may be in the range of between about 4%–6% weight to volume.

The plasma expander and blood substitute may also include a number of cations, alone or in combination. For example, the cations may be provided in the following concentrations: $Na^+$ at 110 to 120 mEq/l, $Ca^{++}$ at about 5 mEq/l, $K^+$ at 0 to 3 mEq/l, and $Mg^{++}$ at 0 to 0.9 mEq/l. These nations may be supplied as dissolved chloride salts. The plasma expander and blood substitute may also include at least one buffer, for example, a lactate and/or bicarbonate buffer. When buffered, the plasma expander will generally be a biological buffer having a buffering capacity in the pH range of about 6.8 to 7.8.

When used in hypovolemic patients, e.g., those that have lost a large volume of blood due to trauma, additional agents may be included in the plasma expander to aid in recovery. Such agents may include, Vitamin K in a concentration of about 1–4 mg/l, amylase, clotting factors, t-PA or even erythropoietin.

In non-medical uses, the exopolysaccharide of the present invention may be used as a chromatography matrix support for purification of chemicals. One such use will be as a suspension solution for use in centrifugation. The exopolysaccharide may even be used in solution as a suspension solution for use in size separation.

The present invention may also be used as a biologically stable, non-toxic material for use in coated plates for a number of biological and analytical uses. Examples of such uses include the coating of tissue culture plates for maintaining the growth, in vitro, of cells. Cells that may be grown on the surface of the exopolysaccharide include prokaryotic and eukaryotic cells. In an analytical setting, the exopolysaccharide disclosed herein may be used as a coating for instrumentation, such as biosensors, that require the maintenance of a biologically compatible environment.

Compositions containing propionic acid and ibuprofen when incorporated into liquid or solid growth media of the LAB-1 strain at a concentration range of 0.1–1.0% (w/v) differentially inhibits its growth, development, cell attachment and biofilm production. Growth of the newly discovered LAB-1 strain as well as its production of mucoidal exopolysaccharide and biofilm may be inhibited or controlled by prodionic acid, derivatives of propionic acid, compounds with related chemical structures or backbones such as 2-(4-isobutylphenyl)-propionic acid, otherwise known as ibuprofen, and solutions, mixtures, suspensions and other kinds of preparations comprising such compounds singly or in combination with other materials and compounds. It would be apparent to one of ordinary skill in the art to apply the above methods to inhibit the production of mucoid compounds and biofilm in any mucoid organism.

A more complete appreciation of the present invention and the scope thereof can be obtained from the accompanying drawings which are briefly summarized below, the following detailed description of the presently-preferred embodiments of the invention, and the appended claims.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE PRESENTLY PREFERRED EXEMPLARY EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLE 1

Characterization of Lab-1 Organism and Exopolysaccharide

Samples of LAB-1 have been deposited under ATCC No. PTA-2500. LAB-1 is a Gram-negative, rod-shaped bacterium isolated by the present inventor from constructed soil samples in the state of Wyoming. The soil sample was constructed by J. Turner at the University Wyoming and contained a contaminant in a background of a *Beijerinckia indica*. The contaminant, LAB-1, was isolated and studied because of its excessive slime production.

A variety of biochemical tests were performed in order to identify the species and the genus of organism. The tests included: assessment of growth conditions, culture appearance, cell appearance and staining characteristics, optimal temperature and pH growth range, oxygen requirements, antibiotic sensitivity testing, tests for catalase and oxidase (using TAXCSN™ disks), amino acid utilization as carbon source, nitrogen fixation, motility test, and a variety of commercially available tests from MICRO-ID™, OXYFERM™, ENTEROTUBE™ and BIOLOG GN MICROPLATE™.

Because the organism was a contaminant in soil amended with a *B. indica* culture, *B. indica* and the LAB-1 organism were grown on plates and total protein profiles were compared by SDS-PAGE. Patty acid analysis was performed by Microbial ID (MIDI) of Newark, Del. who used the high resolution MIDI SHEMLOCK SYSTEM™ to identify fatty acids with high resolution gas chromatography. The same laboratory also sequenced the 16S gene and compared it against the proprietary MICROSEQ™ database (PE APPLIED BIOSYSTE™).

The exopolysaccharide was further analyzed by GLYKO™ (NOVATO™, CA.) fluorophore-assisted carbohydrate electrophoresis (FACE), and matrix-assisted laser desorption/ionization mass spectrometry (MALDI). Immunogenicity of the exopolysaccharide was also tested in mice.

Colonies of LAB-1 on solid medium were irregular with an undulate edge. They exhibited convex elevation, a smooth glistening surface, were white in color and translucent to opaque. The consistency of the colonies was that of a very tenacious and elastic slime. The LAB-1 exopolysaccharide exhibits tremendous tenacity, extending without breakage when pulled with a glass rod over a foot. Due to the production of this exopolysaccharide, it was found difficult to lift the colonies from agar plates.

AB13 culture medium may be used to grow the LAB-1 strain and is made as follows: Per liter of water add 20 g glucose, 1 g NaCl, 1 g yeast extract or 2 g $NaNO_3$, 8 g $K_2HPO_4$, 0.2 g $KH_2PO_4$, 0.5 g $MGSO_4$, and 150 μl 5% $FeCl_2$. To make solid medium, 15 g of agar are added to the medium. This simplified end medium makes large-scale production of the polysaccharide polymer affordable.

Growth in liquid AB13 medium was perfuse and the turbidity was dense and uniform. When the LAB-1 bacterium is grown in liquid medium, the entire solution becomes very viscous with a consistency ranging from that of heavy corn syrup to that of egg whites, depending on the stage of growth. Cultures grown without shaking showed a flocculent deposit along with smooth surface growth. The cultures had a very distinct odor, somewhat sweet smelling, but not pleasant.

Figure 1:
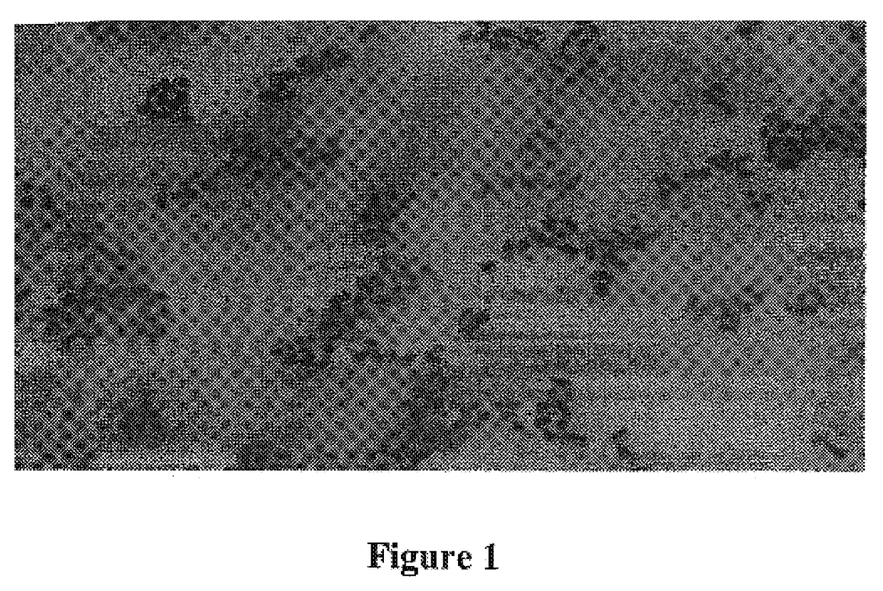
FIG. 1 is a photograph of Gram stained LAB-1 at 100× magnification.

The bacteria were bacilliary with rounded ends and parallel sides and were determined to be Gram negative. There were some irregularities observed in the cell population in cell size, due mainly to length differences, but the average size was about 0.2×0.8 μm. The arrangement of cell packets seemed to be irregular, although a large percentage of cells were aligned side-to-side. The clumping of cells was believed to be due to the tenacious slime layer. The exopolysaccharide could be seen in Gram staining as a light cloud surrounding the cells. FIG. 1 shows the Gram stained cells at 100×. The spore stain showed only red vegetative cells, no spores were observed. The capsule stain showed no capsules, but rather an indefinite exopolysaccharide surrounding the cells. Observation of the stab culture showed that the organism was motile.

Colony morphology on plates grown at 26°, 30°, 37° C. and 45° C. was the same, although growth was optimal at 37° C. Elasticity of the slime layer was also unchanged. Growth was unchanged in liquid AB13 cultures ranging from pH 4, 9 and 11. Growth was not observed at pH 2. Colony morphology on plates was also unchanged over this pH range. The LAB-1 organism was determined to be a facultative anaerobe. various biochemical test results are summarized in the following tables:

TABLE 1

Morphology of LAB-1

| Morphological Characteristics | Results |
|---|---|
| Gram reaction | negative |
| Cell Shape | bacilli |
| Spores | none |
| Growth temp. | 26–37° C. |
| pH range | 4–11 |
| Growth in peptone | + |
| Motility | + |

TABLE 2

| Antibiotic Susceptibility | Results |
|---|---|
| Amikacin | sensitive |
| Ampicillin | resistant |
| Erythromycin | resistant |
| Neomycin | sensitive |
| Novobiocin | sensitive |
| Penicillin | resistant |
| Polymyxin B | sensitive |
| Streptomycin | resistant |
| Taxos A | resistant |
| Tetracycline | sensitive |

TABLE 3

Biochemistry of LAB-1

| Biochemical Properties | Results |
|---|---|
| Adonitol fermentation | + |
| Ammonification | + |
| Arabinose fermentation | + |
| Arginine dihydrolase | + |
| Beta-galactosidase | – |
| Catalase | + |
| Citrate utilization | + |
| Cytochrome oxidase | – |
| Esculin hydrolysis | – |
| Glucose fermentation | + |
| Aerobic glucose | + |
| Anaerobic glucose | + |
| Hydrogen sulfide | – |
| Indole (tryptophanase) | – |
| Inositol fermentation | + |
| Lactose fermentation | + |
| Lysine decarboxylase | – |
| Malonate utilization | – |
| Maltose oxidation | + |
| Mannitol oxidation | + |
| N2 gas production | – |
| Nitrate reductase | – |
| Nitrogen fixation | – |
| Ornithine decarboxylase | – |
| Phenylalanine deaminase | – |
| Sorbitol fermentation | + |
| Sucrose oxidation | – |
| Urease | + |
| VP | + |
| Xylose oxidation | + |

TABLE 4

Carbon Utilization of LAB-1

| Carbon Utilization | Result |
|---|---|
| A-cyclodextrin | + |
| Dextrin | + |
| Glycogen | + |
| Tween 40 | + |
| Tween 80 | + |
| N-acetyl galactosamine | + |
| N-acetyl-D-glucosamine | + |
| Adonitol | + |
| L-arabinose | + |
| D-arabitol | + |
| D-cellubiose | + |
| I-erythritol | – |
| D-fructose | + |
| L-fucose | + |
| D-galactose | + |
| Gentiobiose | +/– |
| A-D-glucose | +/– |
| M-inositol | + |

TABLE 4-continued

Carbon Utilization of LAB-1

| Carbon Utilization | Result |
| --- | --- |
| A-D-lactose | + |
| Lactulose | + |
| Maltose | + |
| D-mannitol | +/− |
| D-mannose | + |
| D-melibiose | + |
| B-methyl-d-glucoside | + |
| D-psicose | + |
| D-raffinose | + |
| L-rhamnose | + |
| D-sorbitol | + |
| Sucrose | + |
| D-trehalose | + |
| Turanose | + |
| Xylitol | + |
| Methyl pyruvate | + |
| Methyl succinate | + |
| Acetic acid | + |
| Cis-aconitic acid | + |
| Itaconic acid | − |
| A-keto-butyric acid | − |
| A-keto-glutaric acid | − |
| A-keto-valeric acid | − |
| D, L-lactic acid | + |
| Malonic acid | + |
| Propionic acid | − |
| Quinic acid | + |
| D-saccharic acid | + |
| Sebacic acid | − |
| Succinic acid | + |
| Bromo Succinic acid | + |
| Succinamic acid | +/− |
| Glucuronamide | + |
| Alaninamide | +/− |
| D-alanine | + |
| L-alanine | + |
| L-alanyl-glycine | + |
| L-asparagine | + |
| L-aspartic acid | + |
| L-glutamic acid | + |
| Glycyl-L-aspartic acid | + |
| Glycyl-L-glutamic acid | + |
| L-histidine | + |
| Hydroxy-L-proline | + |
| L-leucine | − |
| L-ornithine | − |
| L-phenylalanine | − |
| L-proline | + |
| L-pyroglutamic acid | − |
| D-serine | + |
| L-serine | + |
| L-threonine | − |
| Carnitine | − |
| G-amino Butyric acid | + |
| Urocanic acid | − |
| Inosine | + |
| Citric acid | + |
| Formic acid | + |
| D-galactonic acid lactone | + |
| D-galacturonic acid | + |
| D-gluconic acid | + |
| D-glucosaminic acid | + |
| D-glucuronic acid | + |
| A-hydroxybutyric acid | − |
| B-hydroxybutyric acid | + |
| G-hydroxybutyric acid | − |
| P-hydroxphenyl acetic acid | + |
| Uridine | − |
| Thymidine | + |
| Phenylethylamine | − |
| Putrescine | − |
| 2-amino ethanol | − |
| 2,3-butanediol | − |
| Glycerol | + |
| D,L-A-glycerol phosphate | + |
| Glucose-1-phosphate | + |
| Glucose-6-phosphate | + |

Bacteriological information was compiled into the chart shown in Tables 1 through 4. This information was used to search the 9 edition (1994) of *Bergey's Manual of Determinative Bacteriology*. The Bergey's profiles of all Gram negative facultative anaerobic bacilli were researched in an attempt to find potential matches. Special attention was paid to members of the genus Klebsiella because this was the closest match provided by BIOLOG™, and, to the genus Beijerinckia because LAB-1 was isolated as a contaminant amongst a lawn of Beijerinckia colonies.

Although the information contained in Tables 1–4 was considered valuable, this particular method of exploration was quickly proven to be inconclusive. No exact matches were identified, and, the partial matches found were too numerous to consider them all. Therefore, other more concrete methods of identification were utilized.

Because it was entirely possible that LAB-1 could have been a Beijerinckia species, protein profiles of each organism were compared. For the gel in FIG. 2, the colonies of each organism were harvested from AB13 plates and sheared by vortexing with glass beads for five minutes. One volume of running buffer and one volume of bromophenol blue tracking dye was added to the lysate, and the result boiled for five minutes. After a brief spin, the samples were overlaid twice with powdered sucrose to remove cell debris and 100 µl were loaded onto a 4.5% stacking, 10% resolving polyacrylamide gel and run at 30–35 mAmp.

Figure 3:
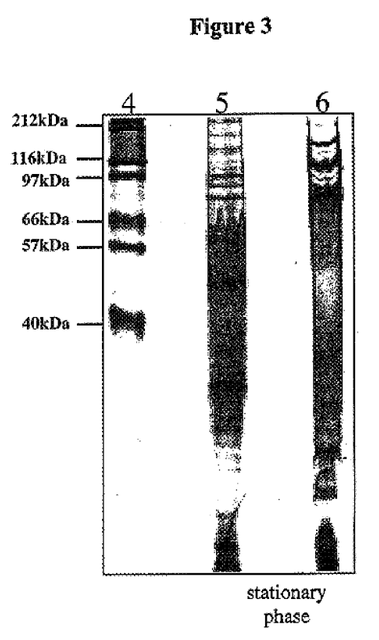
FIG. 3 is a Coomassie stained SDS-PAGE gel of the total protein content of LAB-1 and B. indicia grown in liquid culture.

Samples used for FIG. 3 were grown in liquid AB13 culture. One ml was harvested by pelleting for five minutes, washed with 1% NaCl and again with dH O. Pellets were resuspended in 180 µM of 50 mM Tris, and 10 mM EDTA, pH 8.0. Sixty µl of PSS (4×PSS is 700 µl of 1 M Tris-HCl, pH 6.8, 4.3 g sucrose, 4 mg bromophenol blue, 1.45 µl of 20% SDS, 44 µl of 0.5 M EDTA, 10 mg DTT and dH O to 10 ml) were added to the cells and the mixture was boiled for five minutes. Samples were overlaid with powdered sucrose to remove cell debris and run as above.

Figure 2:
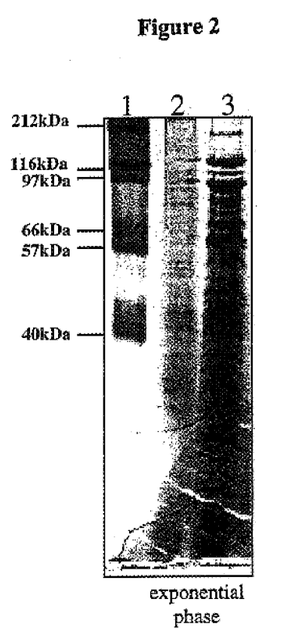
FIG. 2 is a Coomassie stained SDS-PAGE gel of the total protein content of LAB-1 and B. indicia grown on solid culture.

The Coomassie blue stained SDS-PAGE gels shown in FIGS. 2 and 3 clearly demonstrate that there are dissimilarities between the two organisms. It was concluded that the unknown organism LAB-1 was not a Beijerinckia species.

Figure 4A:
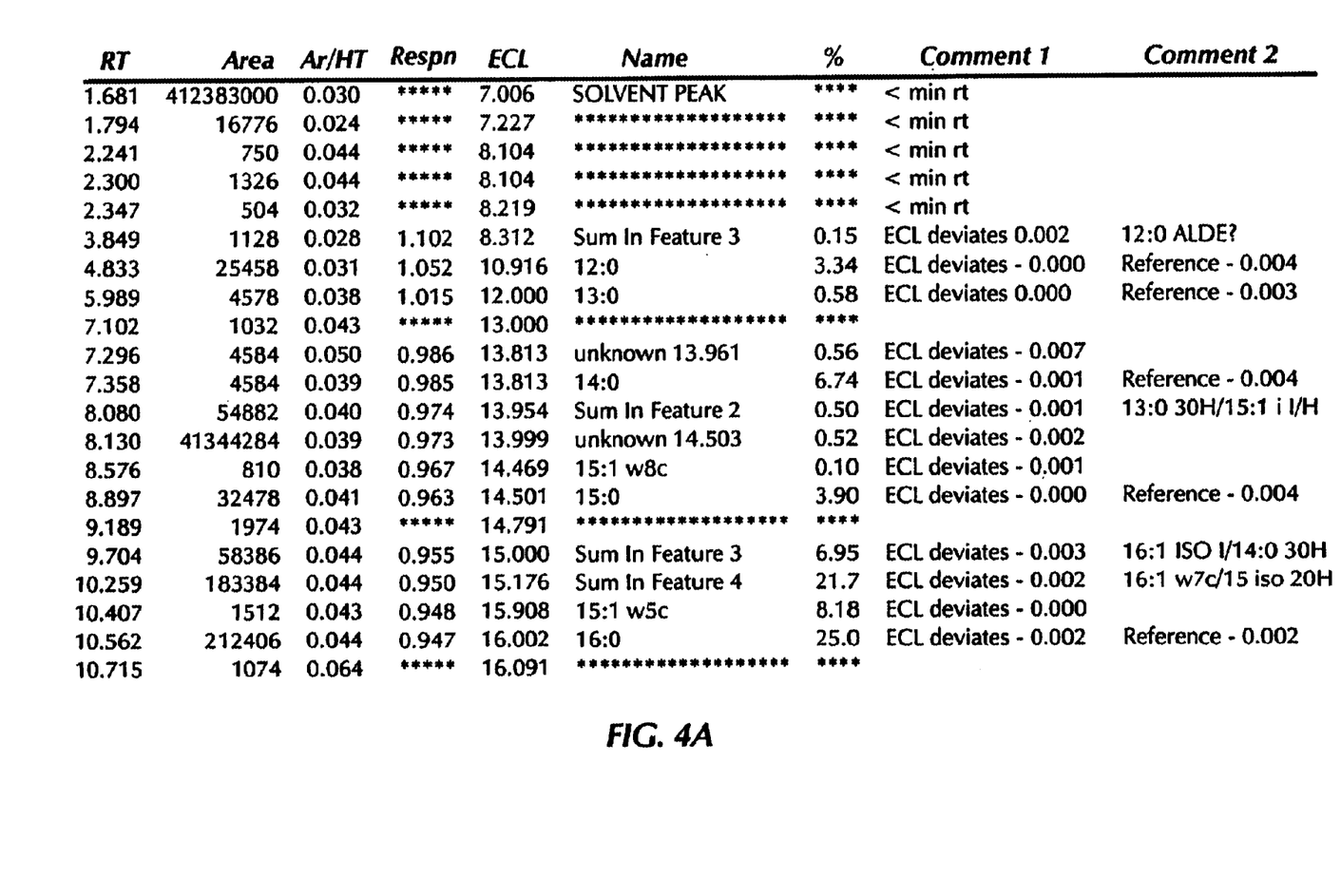
FIG. 4 is the data from gas chromatography of fatty acids in LAB-1.
Figure 4B:
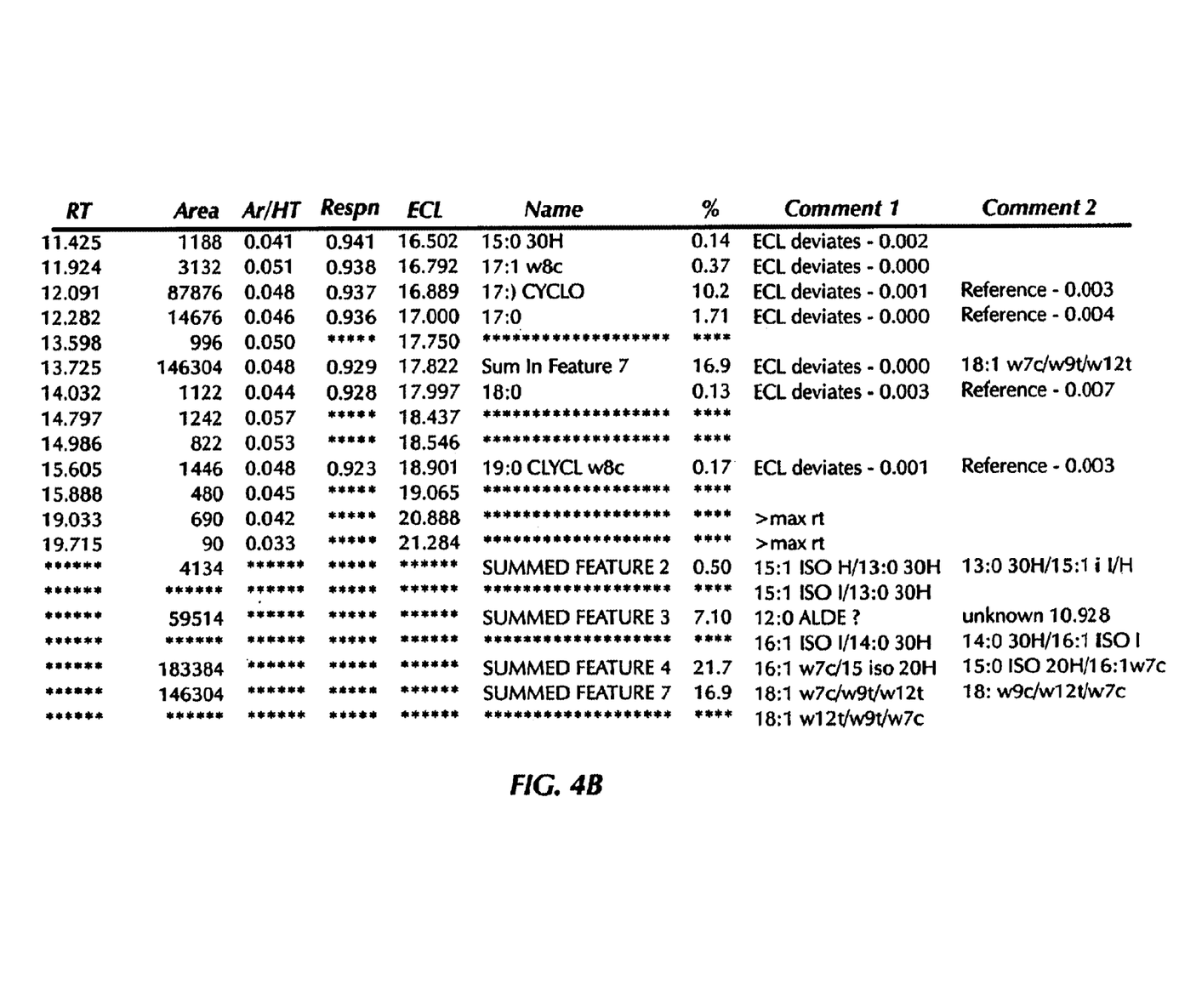
Figure 4C:
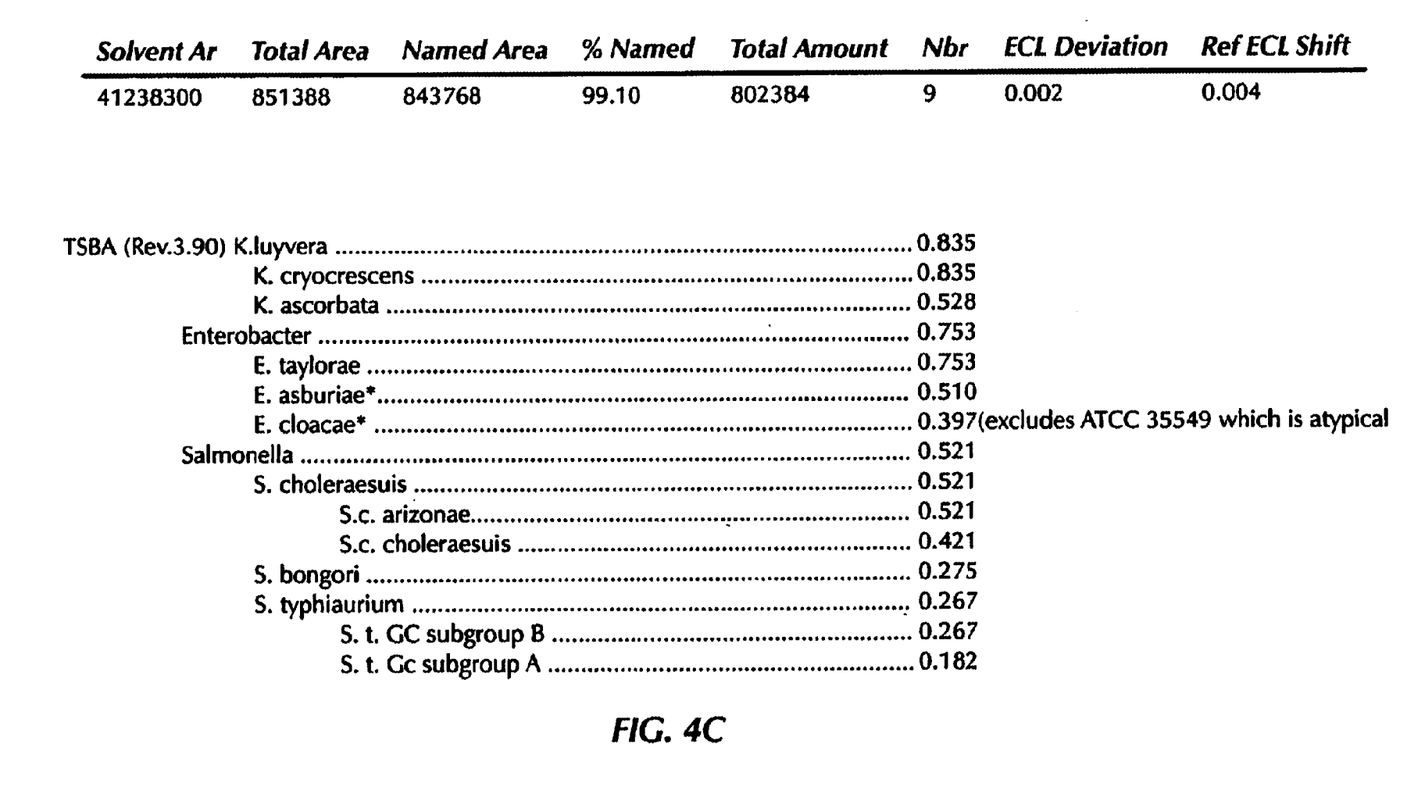

Fatty acid analysis by gas chromatography by MIDI LABS™, Newark, Del., was employed to identify the organism. The growth conditions were standardized, the MIDI SHERLOCK SYSTEM™ was fully automated, and the data compared against proprietary databases containing the fatty acid profiles of more than 1,900 bacteria. The results are shown in FIG. 4. The best match, *Kluyvera cryocrescens*, had a similarity of 0.835. This match would have been considered very good of there had been a separation of at least 0.100 between this first choice and the second choice, *Enterobacter taylorae*, with a similarity of 0.753.

Using these two species, reference was made to the 9 edition (1994) of *Bergey's Manual of Determinative Bacteriology* to compare their characteristics with those listed in Tables 1–4. Also compared was the third choice, *Kluyvera ascorbata*. There were many key differences in the biochemical profiles of LAB-1 and each of the three matches. The properties found to be different amongst these four organisms are shown in Table 5. This information, along with the fatty acid analysis results, led to the conclusion that the organism was not a member of the genus Kluyvera.

TABLE 5

Differences between LAB-1 and K. cryocrescens, K. ascorbata, E. Taylorae

|  | LAB-1 | K. cryo. | K. ascorb. | E. Taylorae |
|---|---|---|---|---|
| Adonitol fermentation | + | − | − | − |
| Arginine dihydrolase | + | − | − | + |
| Esculin hydrolysis | − | + | + | + |
| Indole (tryptophanase) | − | + | + | − |
| Inositol fermentation | + | − | − | − |
| Lactose fermentation | + | + | + | − |
| Lysine decarboxylase | − | − | + | − |
| Melibiose fermentation | + | + | + | − |
| MR | − | + | + | − |
| VP | + | − | − | + |
| Nitrate reductase | − | + | + | + |
| Ornithine decarboxylase | − | + | + | + |
| Raffinose fermentation | + | + | + | − |
| Sorbitol fermentation | + | + | + | − |
| Urease | + | − | − | − |

The next logical step was to determine the 16S rRNA gene sequence. This technique currently is the method of choice for identification purposes. The identification based on the 16S rRNA gene sequence was determined to be *Leclercia adecarboxylata*. The difference in sequence homology between LAB-1 and *L. adecarboxylata* was only 0.59%. Stackebrandt & Goebel, INT'L J. SYSTEM. BACTERIOL. 44: 846 (1994) would consider this a species level match, however the confidence limits of the data obtained by MIDI LABS™ allowed identification only at the genus level. When the biochemical characteristics of LAB-1 and of *L. adecarboxylata* (9$^{th}$ edition Bergey's Manual of Determinative Bacteriology 1994) are compared, there are yet again, numerous differences. The differences led to the questions regarding this method.

TABLE 6

Differences between LAB-1 and L. adecarboxylata

|  | LAB-1 | L. adecarb. |
|---|---|---|
| Arginine dihydrolase | + | − |
| Citrate utilization | + | − |
| Esculin hydrolysis | − | + |
| Glycerol utilization | + | − |
| Indole (tryptophanase) | − | + |
| Inositol fermentation | + | − |
| Malonate utilization | − | + |
| MR | − | + |
| VP | + | − |
| Nitrate reductase | − | + |
| Sorbitol fermentation | + | − |
| Urease | + | − |

Because the same laboratory (MIDI LABS™) produced two different identifications, the validity of both identities was suspect. However, 16S rRNA gene sequencing is considered to be the most reliable method currently available, and, therefore, the identification of *Leclercia adecarboxylata* must be further investigated. With all of the discrepancies that have been encountered, it is reasonable to conclude that this unknown organism (LAB-1) has not been previously identified.

Figure 5:
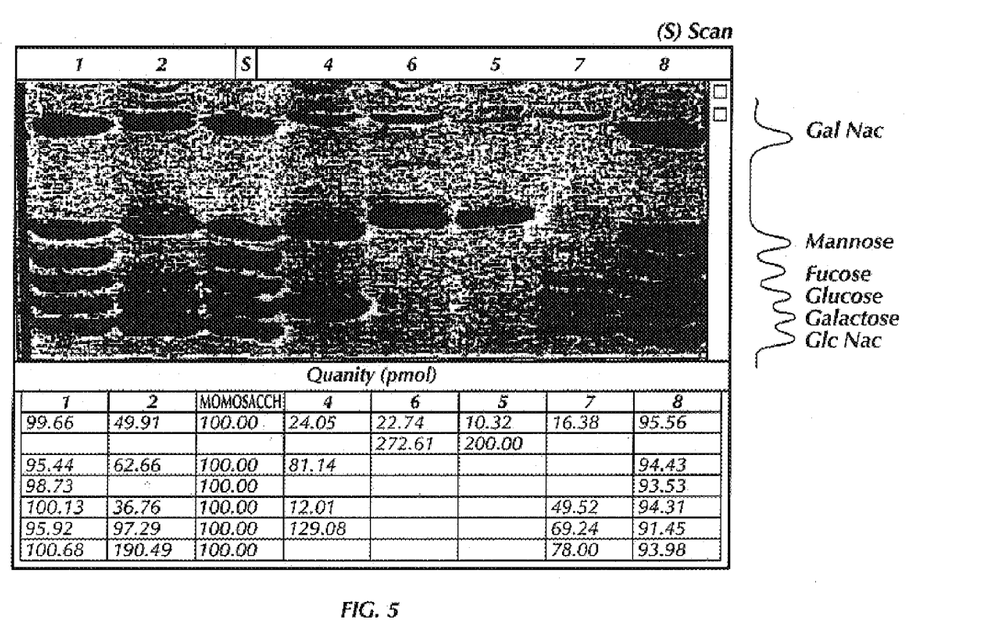
FIG. 5 is a FACE gel showing the sugars identified in the exopolysaccharide produced by LAB-1. Lanes: 1—MONO Ladder Standard 2 (100 pmol ea. monosaccharide); 2—Amine hydrolysis reaction products; 3 [S]—MONO Ladder Standard 2 (100 pmol ea. monosaccharide; scanned for trace shown in [S] Scan); 4—Neutral hydrolysis reaction products; 5—Sialic acid hydrolysis reaction products; 6—NANA labeling control 1 (100 pmol); 7—MONO composition control; 8—MONO Ladder Standard 2 (100 pmol ea. monosaccharide).

Analysis of the exopolysaccharide produced by LAB-1 was by FACE (sugar content) and MALDI (size). Judging from the intensity of the bands shown on the FACE gel in FIG. 5, the amount of fucose present is approximately twice that of galactose; the amount of glucose is approximately 2.5 times that of galactose; and, the amount of mannose is approximately 3 times that of fucose. Therefore, the ratio of galactose:fucose:glucose:mannose is approximately 1:2:3:6. Further investigations regarding the nature and type of linkages and molecular weight determination of the polymer may be undertaken, as will be known to those of skill in the art.

Figure 6A:
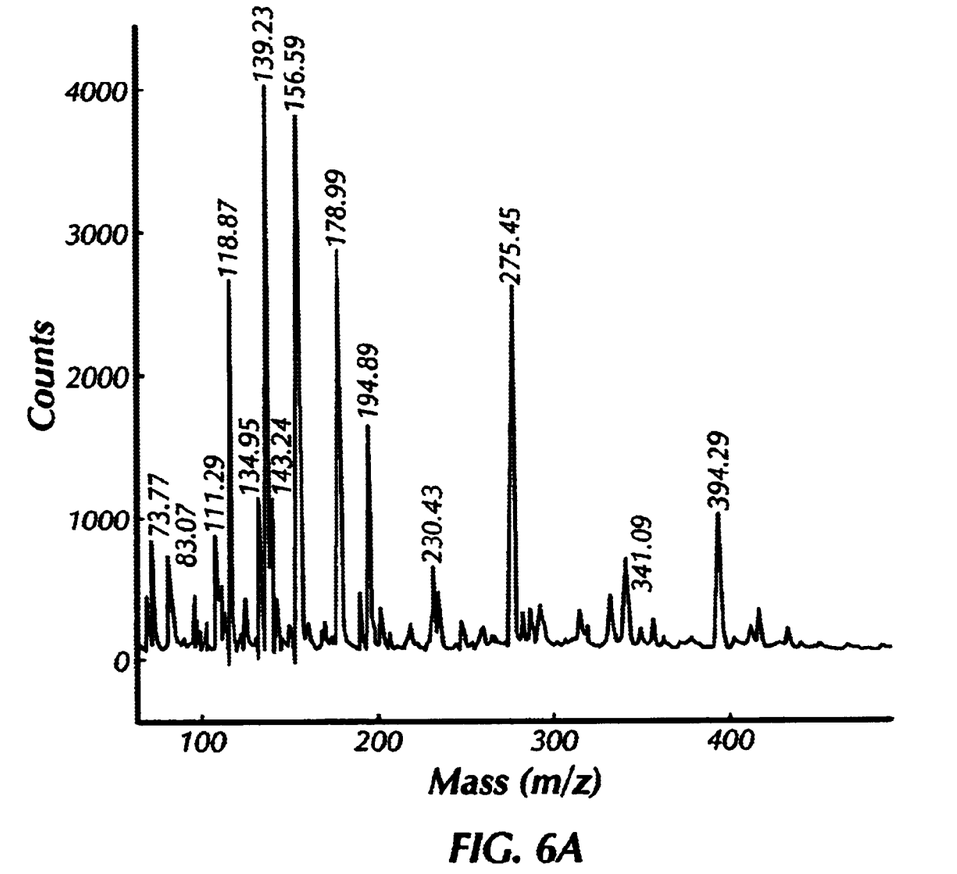
FIG. 6 is a MALDI trace of the exopolysaccharide produced by LAB-1.
Figure 6B:
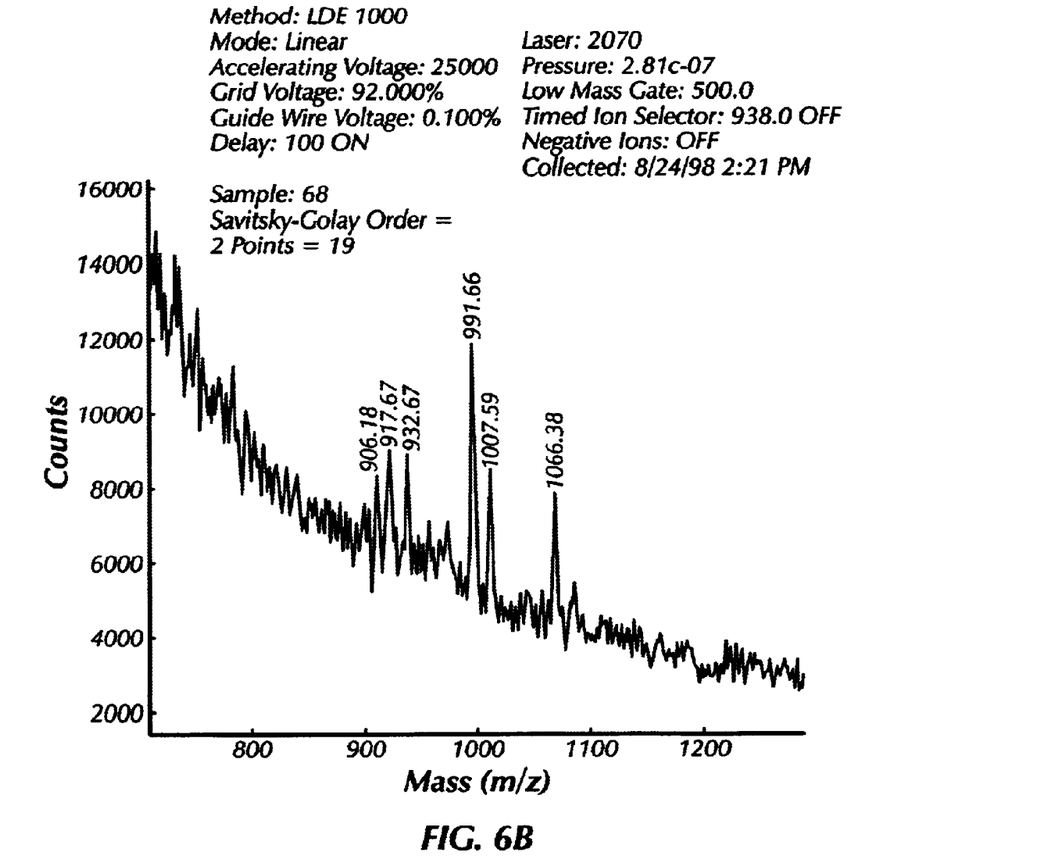

Results of the MALDI study of the exopolysaccharide are shown in FIG. 6. The data indicates that polymerization and depolymerization of the polysaccharide occurred readily as evidenced by the large range of molecular weights found. All monosaccharides identified were neutral sugars that migrate at the same rate as: mannose, fucose, fructose and galactose, acidic sugars that migrate at the same rate as fucose and amine sugars that migrate at the same rate as glucose and fucose. All are six-carbon sugars. This fact makes it impossible to determine the composition of the polymer when only the molecular weight is known. Those substances with molecular weights below 180 are likely breakdown products of the polymer. The largest polymer, molecular weight of 1066.38, was comprised of approximately six 6C sugars.

It was later discovered that the initial exopolysaccharide sample analyzed for immunogenicity in mice contained residual amino acids. The small amount of protein present was from the yeast extract in the media and from dead cells. Even with these amino acids present, it was determined that the exopolysaccharide was non-immunogenic, although a very small immunogenic reaction was observed. This reaction made it necessary to further purify the exopolysaccharide so that it was protein-free.

It was determined that the best way to free the exopolysaccharide of amino acids was to (i) modify the medium to contain no amino acids and (ii) limit growth of the organism to prevent cell death and breakdown. After implementing these two modifications, the exopolysaccharide was found to be free of protein (not shown). The protein-free exopolysaccharide was provided to WASHINGTON BIOTECHNOLOGY™ [St Louis, Mo.] to perform more in-depth studies to determine immunogenic properties. The results were gratifying and the exopolysaccharide immunized rabbits maintained antibody titers of less that 1:110, or non-detectable, for the entire 12 week experiment. In contrast, the inactivated cell-immunized rabbits reached antibody titers as high as 1,638,400. These results are very encouraging because a non-immunogenic biopolymer with tremendous elasticity such as the one characterized in this study probably has numerous industrial, agricultural and biomedical applications.

Much information has been gathered about LAB-1. Unfortunately, its complete identity remains indeterminate. Reliable identification methods have been employed but the results do not agree with each other. It is highly likely that this organism has not been previously identified.

More research is warranted before a definitive identification can be made. Further studies should include direct comparison of LAB-1 with Klebsiella, *Kluyvera cryocrescens* and *Leclercia adecarboxylata*. Methods important to compare these organisms include protein profile determinations and DNA analysis. Results obtained from these approaches will provide good evidence of any phylogenetic relationships.

To further characterize the exopolysaccharide, the monosaccharide linkages and branching of the polysaccharides should be determined. Also, it would be very useful to determine the nature of its overall polymerization. The localization of the gene(s) coding for the polysaccharides may be determined, as will be known to those of skill in the art of molecular biology. Even further studies may be conducted to identify LAB-1, and may include: chromosomal DNA fingerprinting, random primer PCR profiling, rRNA or other gene sequencing, determination of the G+C % content, lipid analysis and BIOLOG™ analysis (a more comprehensive biochemical analysis). Also, detailed studies regarding the chemistry of the polysaccharide will be completed.

EXAMPLE 2

Applications to Engineered Waste Containments and Treatment

The LAB-1 strain may be used to construct environmental biofilm barriers for containment and treatment of contaminated soil and groundwater. The purpose of containment barriers is to control the transport of chemical contaminants from waste disposal facilities or from areas which have become contaminated by spills, industrial processes, illegal dumping or other sources. Several different types of barriers are possible, including the following: (1) subsurface biofilm cutoff wall; (2) subsurface liners consisting of compacted, biofilm treated soil; (3) in-situ biofilm liners; and (4) barriers made by treating geotextiles with biofilm.

The results disclosed herein demonstrate that soil hydraulic conductivity (k) may be reduced by several orders of magnitude by the addition of the biofilm-producing bacterium disclosed herein. The reductions of k obtained using the LAB-1 strain are sufficient to meet Environmental Protection Agency (EPA) criteria for barrier materials, defined as a k value of $10^-$ cm/sec or less. The low hydraulic conductivity persists when the soil is permeated with a variety of chemical solutions, suggesting that a biofilm barrier may be compatible with a wide range of contaminants. The biofilm disclosed herein may also be useful for controlling contaminant transport mechanisms, such as diffusion, adsorption and biodegradation.

Solutions of biofilm and nutrient are pumped into the subsurface through a series of closely-spaced vertical wells. Formation of biofilm in the soil around the wells causes a decrease in soil permeability and decrease in contaminant transport sufficient to form an engineered barrier to contaminant migration. Specific design parameters such as well depth and spacing, pumping pressures, composition of bacterial and nutrient solutions, and time of pumping, are site-specific and depend upon site geology, type and extent of subsurface contamination, ground water conditions, and other variables which must be considered on a case-by-case basis.

Figure 7:
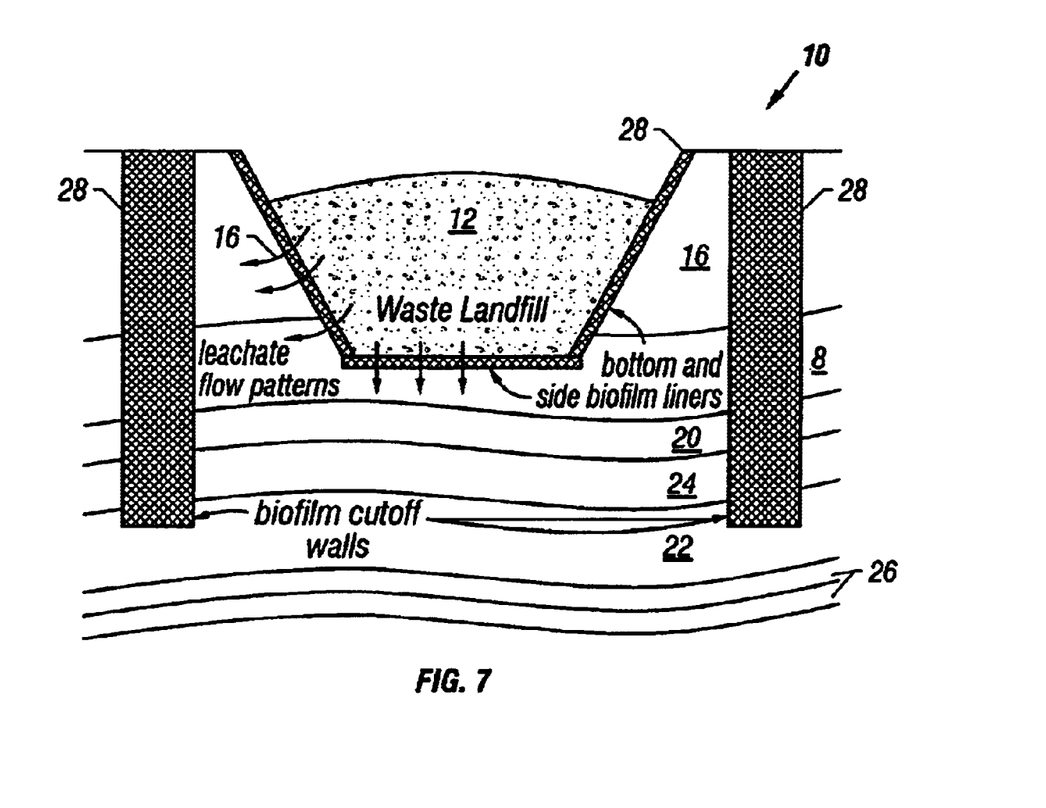
FIG. 7 is a drawing of a cross sectional view of a barrier created with the biofilm of the present invention.

FIG. 7 shows one use of the present invention for the formation of subsurface liners for the containment of wastes in engineered disposal facilities, such as landfills. A landfill 10 is depicted in cross-sectional view. Waste 12 is disposed within a subsurface liner 14. If the liner 14 is being placed during the creation of the landfill 10, a biofilm liner may be used prior to deposition of the liner 14. In addition, a containment wall may be erected that surrounds the waste site, and additional layers of decontaminating biofilm barriers may be included.

In preexisting landfills, such as the one depicted in FIG. 7, waste may leach in the form of a leachate 16 into subsurface strata 18 and 20. A biofilm barrier wall 28 is created that surrounds the waste 12 and captures the leachate 16. The biofilm barrier wall 28 is constructed so as to reach into strata 22, 24 into which the waste 12 does not leach. One advantage of the biofilm of the present invention is that it permits such remedial application to existing landfills that may be leaking and even prevents leachate 16 from reaching a subterranean water layer 26.

Current technology for a biofilm barrier wall 28, for example, may employ fine-grained soils that are field compacted to achieve a hydraulic conductivity of less than $10^-$ cm/sec (commonly referred to as "clay liners"). At many sites, such soil is not readily available and must be transported from off-site, increasing substantially the cost of compacted soil liners. Using the LAB-1 strain of the present invention soil, containment conditions may be met by treating readily available soils with the biofilm in order to achieve the low hydraulic conductivity required for compacted soil liners.

One specific field of use for the LAB-1 biofilms is creating subsurface biofilm liners that include spreading untreated soil in loose (uncompacted) lifts using conventional soil spreading equipment (e.g., bulldozers) Loose lifts will generally be 150 to 225 cm thick. A solution that includes water, LAB-1, and nutrients are applied to the soil, using, e.g., conventional equipment used to apply water to soil (e.g., a truck-mounted water tank with sprinkler hoses). The soil is then compacted using conventional equipment (e.g., sheeps foot rollers) to achieve the specified density, typically resulting in a compacted lift thickness of 100 to 150 cm. The required number of lifts and liner total thickness are site-specific design parameters which are determined by analysis of contaminant transport and regulatory requirements for containment.

Compacted clay liners typically range from 0.6 to 1.3 meters thick. The proposed procedure is similar to field construction of clay liners, except ,hat the soil is treated with a biofilm-producing solution. Alternatively, solutions of strain LAB-1 and nutrients are injected into the ground at a specified depth to create in situ biofilm liners. This type of liner is particularly useful at sites contaminated by accidental spills. Alternatively, previously grown biofilm may be mixed directly into or onto the soil.

Subsurface liners may also be constructed by treating geotextiles with biofilm. Geotextiles are generally made of synthetic fibers that are either woven or matted together, yielding a porous fabric that is used for soil separation, reinforcement, filtration or drainage. Containment barriers can be created by spraying bitumen, rubber-bitumen or other polymeric mixtures into a properly deployed geotextile that contains the LAB-1 produced biofilm disclosed herein. One particular example for use of the LAB-1 biofilm is in the application of a liquid solution containing strain LAB-1 and nutrients to geotextiles to clog the pore spaces and reduce permeability, creating a barrier to flow.

EXAMPLE 3

Materials: Soil and Bacteria

Soil used by the present inventors to analyze waste containment capability is a naturally occurring, easily attainable sand. Based on its grain size distribution and Atterberg limits, this soil is classified as SM, or silty sand of low plasticity, in the Unified Soil Classification System. Permeability tests yield a saturated hydraulic conductivity (k) of approximately $1.5 \times 10^{-5}$ cm/sec when compacted to maximum dry density. This value of k would make the soil unsuitable for use as a waste containment barrier. Initial studies indicated that k could be reduced to values on the order of $10^{-8}$ to $10^{-7}$ cm/sec, which is in the range required for waste containment, by treating this soil with the biofiltm-producing bacterial strain LAB-1.

The operational procedure for use of the LAB-1 bacterium to form a biofilm that may be used to test water permeability may include the following steps: (1) compacting soil into a cylindrical specimen which is placed in a flexible wall permeameter, (2) permeating the specimen with a solution containing LAB-1, and (3) measuring the soil hydraulic conductivity while the specimen is permeated first with nutrient solution, then by water, as is taught by Dennis M. L. and Turner, J. P. J. GEOTECHNICAL & GEOENVIRONMENTAL ENG. 124: 120–127 (1988) (in which a similar procedure was used with the bacterium B. indica).

Using the biofilm produced by the LAB-1 strain disclosed herein, hydraulic conductivity was reduced from $k=1.5 \times 10^{-5}$ to approximately $k=5 \times 10^{-8}$ cm/sec upon establishment of a plugging biofilm, which required permeation with nutrient solution for approximately one week. Most of this decrease occurred within 1 to 2 days, during which the k was reduced to less than $10^{-7}$ cm/sec.

Figure 8:
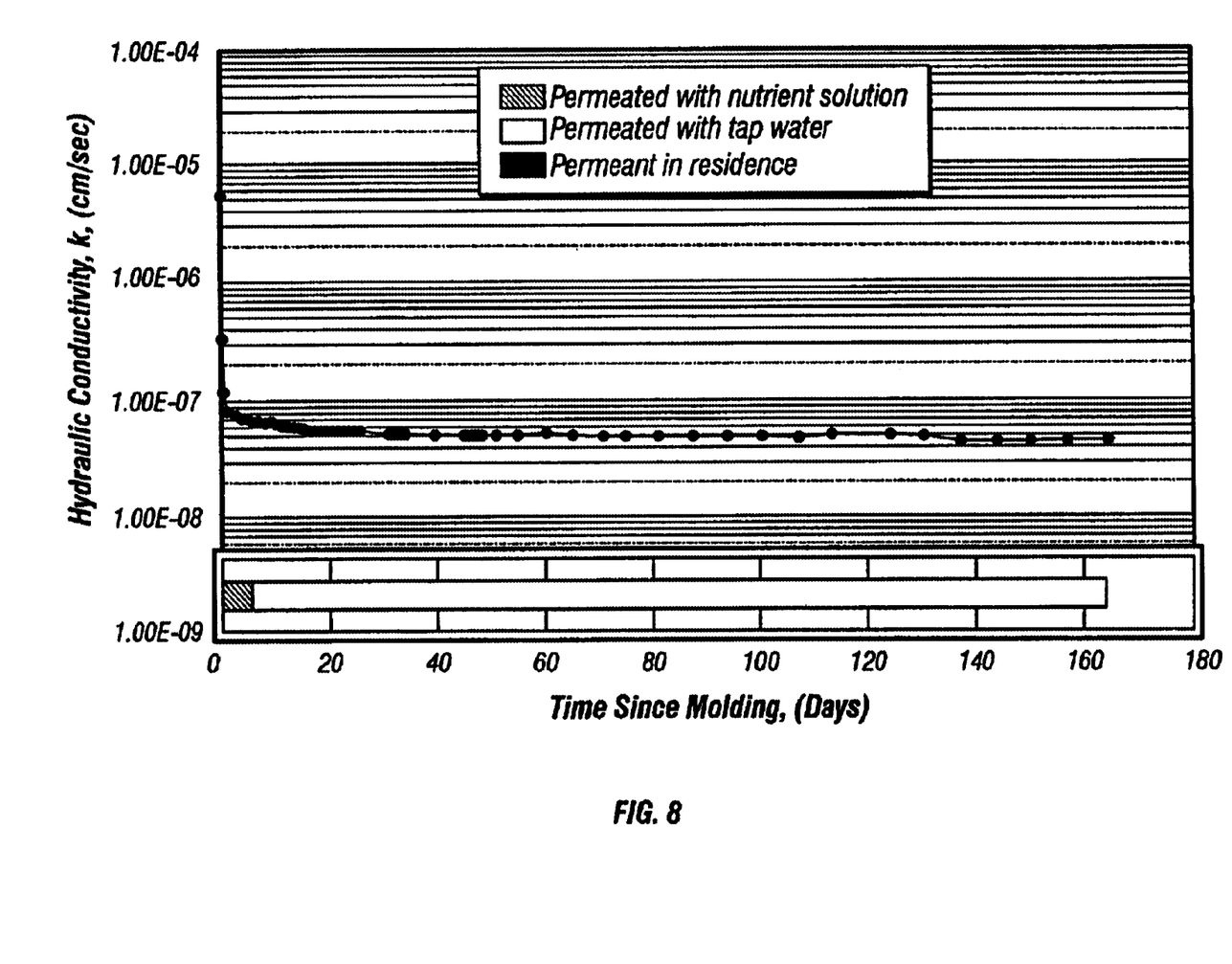
FIG. 8 is a graph of the hydraulic conductivity versus time of a LAB-1 containing biofilm.

FIG. 8 is a graph that shows hydraulic conductivity versus time for a specimen treated with LAB-1. The low hydraulic conductivity persisted for over 160 days, even though the nutrient solution was discontinued after 6 days.

EXAMPLE 4

Applications to Agriculture

Large areas of the earth include desert lands that are not arable without large-scale reclamation. Reclamation in the context of desert lands requires not only irrigation, but extensive soil modification. The economical and social impact of successfully converting non-productive desert land into productive agricultural land is enormous and provides significant benefits to mankind. the use of LAB-1 as a biologically and environmentally sound source of support and nutrients for soil treatment improves the agricultural properties of sandy soils as described herein. Many naturally existing desert soils are aeolian (wind-deposited) and consist of sand and silt sized particles with little or no organic content. Such soils are considered poor for agricultural development because they are highly porous, which promotes rapid infiltration and seepage of irrigation water away from the surface where it is most needed for crops. Lack of organic material generally corresponds to low nutrient content. Many desert areas are active aeolian environments in which wind is the dominant agent of sediment transport.

Agricultural development is severely impacted when topsoil is eroded and transported by wind. Considering the characteristics of sandy desert soils versus the requirements of soils for agriculture, the present invention includes the use of the LAB-1 derived biofilm for the treatment of agricultural soils to improve the following soil agricultural properties: (1) improved water retention characteristics; (2) enhanced ability to establish and support plant growth; and (3) improved erosion resistance. These improvements may be obtained by adding complete or dried and pulverized biofilm, or by the application of LAB-1 strain in bacterial/nutrient solutions using conventional soil watering equipment (e.g., a truck-mounted tank with sprinkler hoses or conventional irrigation systems).

The biofilm of the present invention has been used for the treatment of soil. The biofilm altered the soils properties in many ways that enhanced the soil, s ability to support agriculture. These include the following: (1) an improved ability of sand to retain moisture; (2) an increased biomass in the form of polysaccharides that function as a nutrient supply for plant growth; (3) improved soil cohesion; and(4) increased resistance of soil to erosion.

EXAMPLE 5

Medical Applications

The biofilm of bacterium LAB-1 possesses a number of characteristics that are of potential commercial application in medical devices and treatment, including its low antigenicity, non-toxicity, and its biodegradable nature. For these consumer applications, the exopolysaccharide may be purified, e.g., by the addition of concentrated NaOH to the cell culture at a final concentration of 0.2 M, followed by the addition of 3 volumes of ethanol to precipitate the polymer and other materials. The precipitate is collected and redissolved in half the original volume of water. Protein is removed by either extracting twice with phenol or by ultra-filtration. The aqueous phase is dialyzed, lyophilized and ground to yield a fine white powder as will be known to those skilled in the art.

As the exopolysaccharide is not cell-bound, the exopolysaccharide produced by LAB-1 may, alternatively, be purified without using the alkali treatment or the phenol extraction. Not only is the purification process thereby simplified, it may prevent the removal of alkali-labile acetyl moieties from the purified LAB-1 exopolysaccharide.

Total carbohydrate concentration in culture broths and polymer solutions may be determined by the phenol reaction, described by Gerhardt in Manual of Methods for General Bacteriol. (Amer. Soc. Microbiol., Washington, D.C., 1991). Glucose, galactose and xanthan gum (SIGMA CHEMICAL CO.™, St. Louis, Mo.) may be used as standards. Total protein concentration in culture broths and polymer solutions may be determined using the BIO-RAD™ protein assay (BIO-RAD LASCRATORIES™, Richmond, Calif.) Lysozyne may be used as the standard. Cellular protein may be released by boiling the cells in 0.2 M NaOR.

Purified polysaccharide may be further hydrolyzed 1 M trifluoroacetic acid at 120° C. for times varying between 30 minutes and 2 hours. Monosaccharides in the polysaccharide hydrolysate may be separated using, e.g., a WATERS™ HPLC equipped with a BROWNLEE™ polypore PB, lead loaded cation exchange column, operated at 85° C., with water as the eluent. Detection may be performed by refractive index using, e.g., a WATERS™ Model 401 Differential Refractometer.

The polysaccharide may be further characterized by proton NMR spectroscopy and infrared spectroscopy. Infrared analysis, along with the monosaccharide composition data, may be compared to the composition and IR scans of polysaccharides from mutant or genetically manipulated strains to detect changes in structure.

Being either non- or weakly-immunogenic, the biofilm of the present invention may be used as a vaccine adjuvant or carrier that provides a reservoir for antigens. An adjuvant may be prepared using the LAB-1 derived biofilm of the present invention. Adjuvants may be synthesized by any one of a number of established methods, as has been described by M. Bodansky, et al., "Peptide Synthesis," second edition, Wiley, N.Y. 1976 and R. W. Roeske, Peptides (N.Y.) 3, 102 (1981).

A particularly useful method is the methanesulfonic acid catalyzed esterification procedure described by C. Penney, et al., *J. Organic Chemistry* 50, 1457–1459 (1985). During the preparation of an adjuvant, it may be desirable to temporarily protect reactive functional groups. For example, amines may be protected by urethane-type groups, alcohols by t-butyl or benzyl groups, and acids by ester groups.

The adjuvant may be purified by any of the techniques described previously. One such purification technique is silica gel chromatography, in particular the "flash" (rapid) chromatographic technique, as described by W. Clark Still, et al., *J. Organic Chemistry*, 43, 2923–2925 (1978). Other chromatographic methods, however, including HPLC, may be used for purification of the adjuvant. Crystallization may also be used to purify the adjuvant. In some cases, no purification is required as a product of analytical purity is obtained directly from the synthesis. Methods of formulating the adjuvant into vaccine preparations are well known in the art, and not detailed herein.

As the base bacterium of the present invention does not appear to be a human pathogen, and its exopolysaccharide is not toxic or antigenic and does not readily support bacterial growth, the exopolysaccharide provides an ideal source for oncotic plasma expanders. Furthermore, the exopolysaccharaide's lack of intrinsic antigenicity makes it an ideal candidate for use in, e.g., all mammals. Thus, the present invention includes a mixture of components that, when placed in aqueous solution, may be used to expand the plasma volume of a subject in need thereof.

For purposes of the further description of the invention, the mixture of plasma expanding components according to the invention will be discussed as an aqueous solution. From the following description of the invention it is expected that one ordinarily skilled in the art would be enabled to provide the mixture as a dry mixture and make the adjustments to amounts of sodium chloride, fluid and/or dextrose, etc. as necessary.

The exopolysaccharide oncotic agents of the foregoing mixture of components are ones that are generally water semi-soluble. By water semi-soluble oncotic agent is meant partially-water soluble molecules that when dissolved in the fluid phase of circulating plasma in a living subject are of a size sufficient to prevent their immediate loss from the circulation by traversing the fenestration of the capillary bed into the interstitial spaces of the tissues of the body. The term polysaccharide oncotic agent thus does not include such polysaccharides as chitin, because chitin is not soluble in water.

The plasma expander is made by solubilizing the purified exopolysaccharide in a biocompatible fluid. Plasma expander solutions according to the invention may also contain additional ingredients, including but not limited to, sodium ions (110–120 mEq/1), calcium ions (5 mEq/1), potassium ions (0–3 mEq/1), magnesium ions (0–0.9 mEq/1), and vitamin K (0–10 mg per subject or 0–3 mg/l) Further, the expander may be buffered to about pH 7.4 and may provide assimilable sugar (e.g., dextrose or glucose at 5–10 mM). Preferably, the expander is provided as a sterile solution, but it may also be provided as a powder that can be reconstituted in a sterile manner, or sterilized after reconstitution.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments. All references cited herein are hereby expressly incorporated by reference.

What is claimed is:

1. A method to inhibit the growth and development of bacteria that are characterized as being Gram negative, bacilliary, about 0.2×0.8 μm, facultative anaerobe, grows between 15° and 45° C. with a temperature optimum of 37° C., grows between pH 4–11 but not at pH 2, grows in AB13 medium or minimal medium, is motile, lacks a capsule, lacks and produces an elastic, exopolysaccharide with a sugar content of galactose, fucose, glucose, mannose in a ratio of about 1:2:3:6, which method comprises contacting said bacteria with a composition which comprises propionic acid or a compound containing a propionic acid backbone.

2. A method to inhibit the growth and development of bacteria that produces an exopolysaccharide consisting essentially of neutral sugars migrating at the same rate as mannose, fucose, fructose and galactose, acidic sugars migrating at the same rate as fucose and amine sugars migrating at the same rate as glucose and fucose, wherein the sugar ratio of galactose:fucose:glucose:mannose is about 1:2:3:6, which method comprises contacting said bacteria with a composition which comprises propionic acid or a compound containing a propionic acid backbone.

3. A method to inhibit biofilm production by bacteria that exopolysaccharide, wherein the bacteria are characterized as being Gram negative, bacilliary, about 02×0.8 μm, facultative anaerobe, grows between 15° and 45° C. with a temperature optimum of 37° C. grows between pH 4–11 but not at pH 2, grows in AB13 medium or minimal medium, is motile, lacks a capsule, lacks spore and produces an elastic, exopolysaccharide with a sugar content of galactose, fucose, glucose, mannose in a ratio of about 1:2:3:6, which method comprises contacting said bacteria with a composition wihch comprises propionic acid or a compound containing a propionic acid backbone.

4. A method to inhibit biofilm production by bacteria that excrete a mucoid exopolysaccharide, wherein the bacteria produce an exopolysaccharide consisting essentially of neutral sugars migrating at the same rate as mannose, fucose, fructose and galactose, acidic sugars migrating at the same rate as fucose and amine sugars migrating at the same rate as glucose and fucose, wherein the sugar ratio of galactose:fucose:glucose:mannose is about 1:2:3:6, which method comprises contacting said bacteria with a composition which comprises propionic acid or a compound containing a propionic acid backbone.

5. The method of claim 1, wherein said composition comprises 2-(4-isobutylphenyl)-propionic acid.

6. The method of claim 2, wherein said composition comprises 2-(4-isobutylphenyl)-propionic acid.

7. The method of claim 3, wherein said composition comprises 2-(4-isobutylphenyl)propionic acid.

8. The method of claim 4, wherein said composition comprises 2-(4-isobutylphenyl)-propionic acid.

* * * * *